(12) United States Patent
Cohen et al.

(10) Patent No.: US 7,924,142 B2
(45) Date of Patent: Apr. 12, 2011

(54) PATTERNED SELF-WARMING WIPE SUBSTRATES

(75) Inventors: Jason C. Cohen, Appleton, WI (US);
Dave Allen Soerens, Neenah, WI (US);
John David Amundson, Greenville, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 213 days.

(21) Appl. No.: 12/217,043

(22) Filed: Jun. 30, 2008

(65) Prior Publication Data

US 2009/0325838 A1 Dec. 31, 2009

(51) Int. Cl.
*H04B 3/36* (2006.01)
(52) U.S. Cl. .............. 340/407.1; 340/691.5; 510/142
(58) Field of Classification Search .............. 510/142; 340/573.1, 500–501, 407.1, 691.5
See application file for complete search history.

(56) References Cited

U.S. PATENT DOCUMENTS

| | | | |
|---|---|---|---|
| 2,602,302 A | 7/1952 | Poux | |
| 2,766,478 A | 10/1956 | Raley, Jr. et al. | |
| 3,084,664 A | 4/1963 | Perlman et al. | |
| 3,132,688 A | 5/1964 | Nowak | |
| 3,141,602 A | 7/1964 | Anderson | |
| 3,175,558 A | 3/1965 | Caillonette et al. | |
| 3,199,490 A | 8/1965 | Karlik | |
| 3,261,347 A | 7/1966 | Sherman | |
| 3,338,992 A | 8/1967 | Kinney | |
| 3,341,394 A | 9/1967 | Kinney | |
| 3,363,604 A | 1/1968 | Pschibul | |
| 3,370,630 A | 2/1968 | Haugh et al. | |
| 3,388,953 A | 6/1968 | Browning | |
| 3,502,763 A | 3/1970 | Hartmann | |
| 3,516,941 A | 6/1970 | Matson | |
| 3,542,615 A | 11/1970 | Dobo et al. | |
| 3,585,982 A | 6/1971 | Hollinshead | |
| 3,638,786 A | 2/1972 | Borecki et al. | |
| 3,653,585 A | 4/1972 | Kazaros | |

(Continued)

FOREIGN PATENT DOCUMENTS

CA  2 346 223 A1  8/2001

(Continued)

OTHER PUBLICATIONS

"Phase Change Materials Show Potential for Medical Applications," *Technical Textiles International*, Sep. 1999, pp. 23-26.

(Continued)

*Primary Examiner* — Lynda Salvatore
(74) *Attorney, Agent, or Firm* — R. Joseph Foster, III

(57) ABSTRACT

Generally stated, the present disclosure relates to wiping substrates such as wet wipes and dry wipes that include a thermal grill utilized to deliver a warming sensation. In an exemplary aspect, disposed on at least one structural layer of the wipe substrate is a thermal grill. The thermal grill includes an alternating pattern of thermally active areas and secondary areas that provide a feeling of warmth to a user of the wipe across the entire surface of the wipe. The thermally active portions of the wipe include a temperature change substance that when in liquid communication with an activation agent is adapted to provide a temperature change of at least 5° C. from the temperature of the secondary portion. By providing a thermal grill with thermally active portions, the entire wipe gives the user of the wipe a warming sensation.

18 Claims, 2 Drawing Sheets

U.S. PATENT DOCUMENTS

Figure 1:
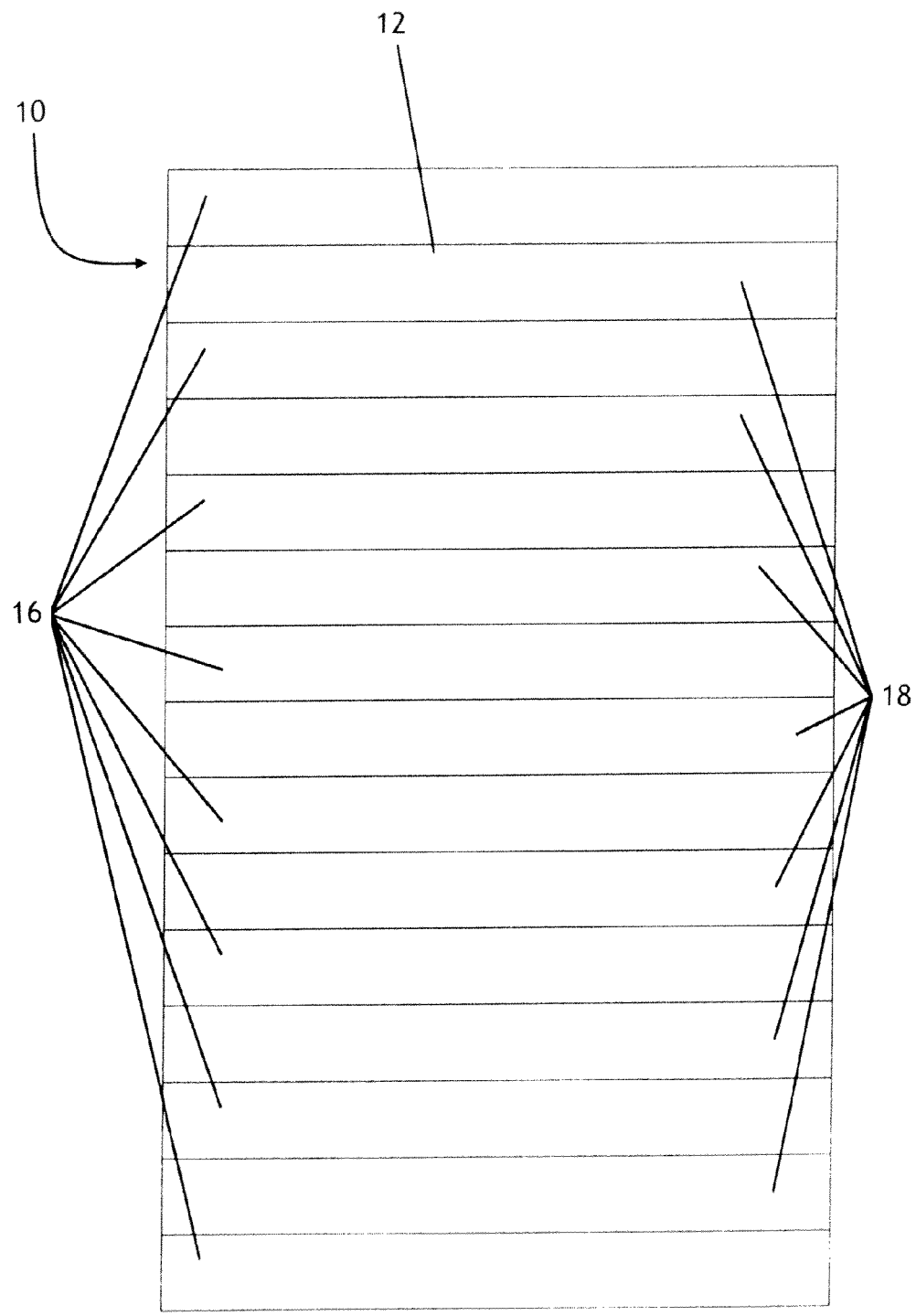

| | | | |
|---|---|---|---|
| 3,676,190 A | 7/1972 | Landler et al. |
| 3,691,270 A | 9/1972 | Charle et al. |
| 3,692,618 A | 9/1972 | Dorschner et al. |
| 3,707,945 A | 1/1973 | Boone |
| 3,756,483 A | 9/1973 | Schraeder |
| 3,802,817 A | 4/1974 | Matsuki et al. |
| 3,804,061 A | 4/1974 | Cassar et al. |
| 3,849,241 A | 11/1974 | Butin et al. |
| 3,865,271 A | 2/1975 | Gold |
| 3,900,035 A | 8/1975 | Welch et al. |
| 3,980,203 A | 9/1976 | Dearling |
| 4,041,900 A | 8/1977 | Charles |
| 4,100,324 A | 7/1978 | Anderson et al. |
| 4,106,433 A | 8/1978 | Fernando et al. |
| 4,106,616 A | 8/1978 | Boone |
| 4,132,771 A | 1/1979 | Schreiber et al. |
| 4,159,316 A | 6/1979 | Januszewski et al. |
| 4,340,563 A | 7/1982 | Appel et al. |
| 4,362,715 A | 12/1982 | Strianse et al. |
| 4,375,448 A | 3/1983 | Appel et al. |
| 4,379,143 A | 4/1983 | Sherry et al. |
| 4,381,058 A | 4/1983 | Chaussadas et al. |
| 4,407,957 A | 10/1983 | Lim |
| 4,436,224 A | 3/1984 | McInerny |
| 4,462,224 A | 7/1984 | Dunshee et al. |
| 4,516,564 A | 5/1985 | Koiso et al. |
| 4,585,002 A | 4/1986 | Kissin |
| 4,596,250 A | 6/1986 | Beisang, III et al. |
| 4,598,664 A | 7/1986 | Hamlin |
| 4,620,502 A | 11/1986 | Kimble |
| 4,626,550 A | 12/1986 | Hertzenberg |
| 4,667,846 A | 5/1987 | Marceau |
| 4,696,050 A | 9/1987 | Sengewald |
| 4,704,116 A | 11/1987 | Enloe |
| 4,747,365 A | 5/1988 | Tusch |
| 4,756,299 A | 7/1988 | Podella |
| 4,781,193 A | 11/1988 | Pagden |
| 4,798,603 A | 1/1989 | Meyer et al. |
| 4,798,691 A | 1/1989 | Kasai et al. |
| 4,860,748 A | 8/1989 | Chiurco et al. |
| 4,872,442 A | 10/1989 | Manker |
| 4,878,764 A | 11/1989 | Meyer |
| 4,886,063 A | 12/1989 | Crews |
| 4,904,524 A | 2/1990 | Yoh |
| 4,940,464 A | 7/1990 | Van Gompel et al. |
| 4,964,543 A | 10/1990 | Scheiber |
| 4,966,286 A | 10/1990 | Muckenfuhs |
| 4,981,135 A | 1/1991 | Hardy |
| 4,984,530 A | 1/1991 | Dutton |
| 4,991,538 A | 2/1991 | Davids et al. |
| 5,035,321 A | 7/1991 | Denton |
| 5,036,978 A | 8/1991 | Frank et al. |
| 5,045,569 A | 9/1991 | Delgado |
| 5,048,687 A | 9/1991 | Suzuki et al. |
| 5,067,612 A | 11/1991 | Tsuchiya et al. |
| 5,071,706 A | 12/1991 | Soper |
| 5,163,558 A | 11/1992 | Palumbo et al. |
| 5,167,655 A | 12/1992 | McCoy |
| 5,176,672 A | 1/1993 | Bruemmer et al. |
| 5,180,637 A | 1/1993 | Sumii |
| 5,194,356 A | 3/1993 | Sacripante et al. |
| 5,213,881 A | 5/1993 | Timmons et al. |
| 5,232,118 A | 8/1993 | Samuel |
| 5,265,509 A | 11/1993 | Chen |
| 5,266,592 A | 11/1993 | Grub et al. |
| 5,282,687 A | 2/1994 | Yee |
| 5,284,703 A | 2/1994 | Everhart et al. |
| 5,348,750 A | 9/1994 | Greenberg |
| 5,350,624 A | 9/1994 | Georger et al. |
| 5,361,905 A | 11/1994 | McQueeny et al. |
| 5,364,382 A | 11/1994 | Latimer et al. |
| 5,366,801 A | 11/1994 | Bryant et al. |
| 5,375,616 A | 12/1994 | Chen |
| 5,392,945 A | 2/1995 | Syrek |
| 5,415,222 A | 5/1995 | Colvin et al. |
| 5,415,624 A | 5/1995 | Williams |
| 5,418,062 A | 5/1995 | Budd |
| 5,425,975 A | 6/1995 | Koiso et al. |
| 5,435,465 A | 7/1995 | El Amin |
| 5,439,104 A | 8/1995 | Wolska Klis |
| 5,443,084 A | 8/1995 | Saleur |
| 5,467,894 A | 11/1995 | Altonen et al. |
| 5,484,895 A | 1/1996 | Meister et al. |
| 5,486,166 A | 1/1996 | Bishop et al. |
| 5,490,846 A | 2/1996 | Ellis et al. |
| 5,509,915 A | 4/1996 | Hanson et al. |
| 5,538,531 A | 7/1996 | Hudson et al. |
| 5,545,197 A | 8/1996 | Bowen |
| 5,598,954 A | 2/1997 | Salzano |
| 5,618,008 A | 4/1997 | Dearwester et al. |
| 5,624,025 A | 4/1997 | Hixon |
| 5,628,769 A | 5/1997 | Saringer |
| 5,637,389 A | 6/1997 | Colvin et al. |
| 5,649,914 A | 7/1997 | Glaug et al. |
| 5,656,708 A | 8/1997 | Meister |
| 5,677,048 A | 10/1997 | Pushaw |
| 5,681,298 A | 10/1997 | Brunner et al. |
| 5,712,212 A | 1/1998 | Scott et al. |
| 5,722,774 A | 3/1998 | Hartz |
| 5,728,454 A | 3/1998 | Inaba et al. |
| 5,733,272 A | 3/1998 | Brunner et al. |
| 5,738,082 A | 4/1998 | Page et al. |
| 5,747,004 A | 5/1998 | Giani et al. |
| 5,762,710 A | 6/1998 | Ngai et al. |
| 5,766,389 A | 6/1998 | Brandon et al. |
| 5,780,047 A | 7/1998 | Kamiya et al. |
| 5,785,179 A | 7/1998 | Buczwinski et al. |
| 5,785,980 A | 7/1998 | Mathewson |
| 5,792,213 A | 8/1998 | Bowen |
| 5,819,989 A | 10/1998 | Saraceni |
| 5,820,973 A | 10/1998 | Dodge, II et al. |
| 5,839,608 A | 11/1998 | Gillberg LaForce |
| 5,887,759 A | 3/1999 | Ayigbe |
| 5,944,709 A | 8/1999 | Barney et al. |
| 5,951,762 A | 9/1999 | Shangold et al. |
| 5,967,665 A | 10/1999 | MacDonald et al. |
| 5,975,074 A | 11/1999 | Koiso et al. |
| 5,993,433 A | 11/1999 | St. Louis et al. |
| 6,057,372 A | 5/2000 | Nobuhiro et al. |
| 6,059,882 A | 5/2000 | Steinhardt et al. |
| 6,085,899 A | 7/2000 | Thorsbakken |
| 6,096,067 A | 8/2000 | Cramer et al. |
| 6,121,165 A | 9/2000 | Mackey et al. |
| 6,127,294 A | 10/2000 | Koiso et al. |
| 6,171,647 B1 | 1/2001 | Holman |
| 6,180,124 B1 | 1/2001 | Ohta et al. |
| 6,213,645 B1 | 4/2001 | Beer |
| 6,216,920 B1 | 4/2001 | Baggett |
| 6,217,717 B1 | 4/2001 | Drummond et al. |
| 6,217,889 B1 | 4/2001 | Lorenzi et al. |
| 6,248,097 B1 | 6/2001 | Beitz et al. |
| 6,248,125 B1 | 6/2001 | Helming |
| 6,267,975 B1 | 7/2001 | Smith, III et al. |
| 6,287,580 B1 | 9/2001 | Gott et al. |
| 6,308,341 B1 | 10/2001 | Shelton |
| 6,314,971 B1 | 11/2001 | Schneider |
| 6,318,555 B1 | 11/2001 | Kuske et al. |
| 6,319,318 B1 | 11/2001 | Pekarek et al. |
| 6,321,937 B1 | 11/2001 | DeSimone et al. |
| 6,322,801 B1 | 11/2001 | Lorenzi et al. |
| 6,333,109 B1 | 12/2001 | Harada et al. |
| 6,343,491 B1 | 2/2002 | Jung |
| 6,346,153 B1 | 2/2002 | Lake et al. |
| 6,387,385 B1 | 5/2002 | Wang |
| 6,397,560 B1 | 6/2002 | Weder |
| 6,401,968 B1 | 6/2002 | Huang et al. |
| 6,431,111 B1 | 8/2002 | Zhang |
| 6,436,128 B1 | 8/2002 | Usui |
| 6,457,434 B1 | 10/2002 | Lazar |
| 6,484,514 B1 | 11/2002 | Joseph et al. |
| 6,503,976 B2 | 1/2003 | Zuckerman et al. |
| 6,520,942 B1 | 2/2003 | Putman |
| 6,528,766 B1 | 3/2003 | Parks et al. |
| 6,547,063 B1 | 4/2003 | Zaveri et al. |
| 6,547,881 B1 | 4/2003 | Klöckner |
| 6,550,633 B2 | 4/2003 | Huang et al. |
| 6,561,696 B1 | 5/2003 | Rusnak et al. |

| | | |
|---|---|---|
| 6,567,696 B2 | 5/2003 | Voznesensky et al. |
| 6,592,004 B2 | 7/2003 | Huang et al. |
| 6,598,103 B2 | 7/2003 | MacWilliams et al. |
| 6,601,705 B2 | 8/2003 | Molina et al. |
| 6,601,737 B1 | 8/2003 | Sandler |
| 6,613,144 B1 | 9/2003 | Loertscher et al. |
| 6,626,570 B2 | 9/2003 | Fox et al. |
| 6,642,427 B2 | 11/2003 | Roe et al. |
| 6,645,190 B1 | 11/2003 | Olson et al. |
| 6,658,432 B1 | 12/2003 | Alavi et al. |
| 6,663,686 B1 | 12/2003 | Geiger et al. |
| 6,673,358 B1 | 1/2004 | Cole et al. |
| 6,680,084 B1 | 1/2004 | Chtourou |
| 6,708,823 B2 | 3/2004 | Cottingham et al. |
| 6,708,845 B2 | 3/2004 | Weng |
| 6,749,148 B2 | 6/2004 | Helfer Grand |
| 6,752,998 B2 | 6/2004 | Verdrel Lahaxe et al. |
| 6,770,064 B1 | 8/2004 | Ruscher |
| 6,791,004 B2 | 9/2004 | Sprengard Eichel et al. |
| 6,827,080 B2 | 12/2004 | Fish et al. |
| 6,831,051 B2 | 12/2004 | Sommerville Roberts et al. |
| 6,838,154 B1 | 1/2005 | Varona et al. |
| 6,847,011 B2 | 1/2005 | McConnell et al. |
| 6,866,145 B2 | 3/2005 | Richards et al. |
| 6,868,666 B2 | 3/2005 | Frank et al. |
| 6,869,441 B2 | 3/2005 | Agarwal et al. |
| 6,881,219 B1 | 4/2005 | Agarwal et al. |
| 6,881,792 B2 | 4/2005 | Harada et al. |
| 6,890,553 B1 | 5/2005 | Sun et al. |
| 6,890,592 B2 | 5/2005 | Seehafer et al. |
| 6,903,307 B1 | 6/2005 | McConnell et al. |
| 6,918,513 B1 | 7/2005 | Downey |
| 6,946,413 B2 | 9/2005 | Lange et al. |
| 6,952,849 B2 | 10/2005 | Pacella |
| 6,958,103 B2 | 10/2005 | Anderson et al. |
| 6,960,349 B2 | 11/2005 | Shantz et al. |
| 7,008,620 B2 | 3/2006 | Sun et al. |
| 7,021,848 B1 | 4/2006 | Gruenbacher et al. |
| 7,083,839 B2 | 8/2006 | Fish et al. |
| 7,321,309 B2 | 1/2008 | Cohen |
| 7,517,582 B2 | 4/2009 | Amundson et al. |
| 7,597,954 B2 | 10/2009 | Amundson et al. |
| 2002/0050659 A1 | 5/2002 | Toreki et al. |
| 2002/0192268 A1 | 12/2002 | Alwattari et al. |
| 2003/0082217 A1 | 5/2003 | Afriat et al. |
| 2003/0084914 A1 | 5/2003 | Simon |
| 2003/0105192 A1 | 6/2003 | Li et al. |
| 2003/0175517 A1 | 9/2003 | Voigt et al. |
| 2003/0232090 A1 | 12/2003 | Ahmad et al. |
| 2004/0062732 A1 | 4/2004 | Friscia et al. |
| 2004/0063603 A1 | 4/2004 | Dave et al. |
| 2004/0069298 A1 | 4/2004 | Minami |
| 2004/0084791 A1 | 5/2004 | Han et al. |
| 2004/0116017 A1 | 6/2004 | Smith, III et al. |
| 2004/0118862 A1 | 6/2004 | Amundson |
| 2004/0121072 A1 | 6/2004 | Xing et al. |
| 2004/0127880 A1 | 7/2004 | Weber |
| 2004/0164085 A1 | 8/2004 | Kitching et al. |
| 2004/0169299 A1 | 9/2004 | Davis et al. |
| 2004/0254550 A1 | 12/2004 | Huang et al. |
| 2004/0265589 A1 | 12/2004 | Yamada et al. |
| 2005/0033251 A1 | 2/2005 | Toreki et al. |
| 2005/0048090 A1 | 3/2005 | Rau |
| 2005/0053647 A1 | 3/2005 | Matusch et al. |
| 2005/0067423 A1 | 3/2005 | Cho |
| 2005/0067726 A1 | 3/2005 | Yan et al. |
| 2005/0113771 A1 | 5/2005 | MacDonald et al. |
| 2005/0136765 A1 | 6/2005 | Shannon |
| 2005/0169868 A1 | 8/2005 | Mohammadi et al. |
| 2005/0226834 A1 | 10/2005 | Lambino et al. |
| 2005/0250169 A1 | 11/2005 | Gonzalez et al. |
| 2006/0003649 A1 | 1/2006 | Runge et al. |
| 2006/0008621 A1 | 1/2006 | Gusky et al. |
| 2006/0018953 A1 | 1/2006 | Guillon et al. |
| 2006/0141882 A1 | 6/2006 | Quincy et al. |
| 2006/0236998 A1 | 10/2006 | Cohen |
| 2006/0252899 A1 | 11/2006 | Himori et al. |
| 2006/0270585 A1 | 11/2006 | Jordan et al. |
| 2006/0270586 A1 | 11/2006 | Jordan et al. |
| 2006/0276356 A1 | 12/2006 | Panandiker et al. |
| 2007/0049881 A1 | 3/2007 | Ales et al. |
| 2007/0142797 A1 | 6/2007 | Long et al. |
| 2007/0252712 A1 | 11/2007 | Allen et al. |
| 2008/0045913 A1 | 2/2008 | Johnson et al. |
| 2008/0140165 A1* | 6/2008 | Cohen et al. .................. 607/108 |
| 2008/0145437 A1* | 6/2008 | Amundson et al. ........... 424/490 |

FOREIGN PATENT DOCUMENTS

| | | |
|---|---|---|
| DE | 29 12 972 C2 | 8/1982 |
| DE | 31 01 474 A1 | 8/1982 |
| DE | 34 47 833 A1 | 7/1986 |
| DE | 35 35 330 A1 | 4/1987 |
| DE | 39 22 159 A1 | 1/1991 |
| DE | 197 16 254 A1 | 1/1999 |
| DE | 199 20 685 A1 | 11/2000 |
| DE | 199 37 884 A1 | 2/2001 |
| DE | 100 02 590 A1 | 8/2001 |
| DE | 201 08 351 U1 | 10/2001 |
| DE | 100 26 453 A1 | 11/2001 |
| DE | 102 34 257 A1 | 2/2004 |
| EP | 0 077 005 A1 | 4/1983 |
| EP | 0 288 909 A1 | 11/1988 |
| EP | 0 351 907 A2 | 1/1990 |
| EP | 0 370 600 A1 | 5/1990 |
| EP | 0 252 553 B1 | 3/1991 |
| EP | 0 863 240 A1 | 9/1998 |
| EP | 0 865 755 A1 | 9/1998 |
| EP | 0 897 719 A1 | 2/1999 |
| EP | 0 953 312 A1 | 11/1999 |
| EP | 1 038 793 A1 | 9/2000 |
| EP | 1 166 866 A2 | 1/2002 |
| EP | 1 181 911 A1 | 2/2002 |
| EP | 1 186 286 A1 | 3/2002 |
| EP | 1 191 092 A1 | 3/2002 |
| EP | 1 229 097 A1 | 8/2002 |
| EP | 1 247 568 A1 | 10/2002 |
| EP | 1 334 921 A2 | 8/2003 |
| EP | 0 994 650 B1 | 2/2004 |
| EP | 1 051 478 B1 | 11/2004 |
| EP | 1 479 432 A1 | 11/2004 |
| EP | 1 495 704 A1 | 1/2005 |
| FR | 2 669 205 A1 | 5/1992 |
| FR | 2 823 137 A1 | 10/2002 |
| GB | 1 370 633 A | 10/1974 |
| GB | 2 168 031 A | 6/1986 |
| GB | 2 192 171 A | 1/1988 |
| GB | 2 297 490 A | 8/1996 |
| JP | 08-112303 A | 5/1996 |
| JP | 08-173471 A | 7/1996 |
| JP | 2002-020739 A | 1/2002 |
| WO | WO 93/04622 A1 | 3/1993 |
| WO | WO 99/24159 A1 | 5/1999 |
| WO | WO 00/37009 A2 | 6/2000 |
| WO | WO 00/43286 A1 | 7/2000 |
| WO | WO 01/06903 A1 | 2/2001 |
| WO | WO 01/08658 A1 | 2/2001 |
| WO | WO 01/10366 A1 | 2/2001 |
| WO | WO 01/12147 A1 | 2/2001 |
| WO | WO 01/12148 A1 | 2/2001 |
| WO | WO 01/12149 A1 | 2/2001 |
| WO | WO 01/35906 A2 | 5/2001 |
| WO | WO 01/39704 A1 | 6/2001 |
| WO | WO 01/42117 A1 | 6/2001 |
| WO | WO 01/54661 A1 | 8/2001 |
| WO | WO 01/64525 A2 | 9/2001 |
| WO | WO 01/76439 A1 | 10/2001 |
| WO | WO 01/89353 A1 | 11/2001 |
| WO | WO 02/01129 A1 | 1/2002 |
| WO | WO 02/06421 A1 | 1/2002 |
| WO | WO 02/064069 A2 | 8/2002 |
| WO | WO 03/000487 A2 | 1/2003 |
| WO | WO 03/005876 A1 | 1/2003 |
| WO | WO 03/018186 A1 | 3/2003 |
| WO | WO 03/028515 A1 | 4/2003 |
| WO | WO 03/048654 A1 | 6/2003 |
| WO | WO 03/049939 A1 | 6/2003 |
| WO | WO 03/059139 A1 | 7/2003 |
| WO | WO 03/094644 A1 | 11/2003 |

| WO | WO 03/099427 A1 | 12/2003 |
| WO | WO 2004/014540 A1 | 2/2004 |
| WO | WO 2004/016234 A1 | 2/2004 |
| WO | WO 2004/043311 A1 | 5/2004 |
| WO | WO 2004/047977 A1 | 6/2004 |
| WO | WO 2004/084782 A1 | 10/2004 |
| WO | WO 2004/108075 A2 | 12/2004 |
| WO | WO 2005/011855 A1 | 2/2005 |
| WO | WO 2005/011856 A1 | 2/2005 |
| WO | WO 2005/018514 A1 | 3/2005 |
| WO | WO 2005/018795 A1 | 3/2005 |
| WO | WO 2005/055790 A1 | 6/2005 |
| WO | WO 2005/087068 A1 | 9/2005 |

OTHER PUBLICATIONS

Acree Jr., William E., "Enthalpy of Fusion of Some Organic Compounds," *CRC Handbook of Chemistry and Physics*, 72nd Ed., 1991-92, pp. 5-83 to 5-90.

Ahlstrom, B. et al., "Loss of Bactericidal Capacity of Long-chain Quaternary Ammonium Compounds with Protein at Lowered Temperature," *APMIS*, vol. 107, No.6, Jun. 1999, pp. 606-614.

Ahlstrom, B. et al., "The Effect of Hydrocarbon Chain Length, pH, and Temperature on the Binding and Bactericidal Effect of Amphiphilic Betaine Esters on *Salmonella typhimurium*," *APMIS*, vol. 107, No. 3, Mar. 1999, pp. 318-324.

Akiyama, H. et al., "Antimicrobial Effects of Acidic Hot-Spring Water on *Staphlycococcus aureus* Strains Isolated from Atopic Dermatitis Patients," *Journal of Dermatological.Science*, vol. 24, No. 2, Nov. 2000, pp. 112-118.

Bengoechea, J. et al., "Temperature-Regulated Efflux Pump/Potassium Antiporter System Mediates Resistance to Cationic Antimicrobial Peptides in *Yersinia*," *Molecular Microbiology*, vol. 37, No. 1, Jul. 2000, pp. 67-80.

Blouin, Jean-Sebastian et al., "Postural Stability is Altered by the Stimulation of Pain But Not Warm Receptors in Humans," *BMC Musculoskeletal Disorders*, vol. 4, No. 1, BioMed Central, London, GB, Oct. 17, 2003, pp. 1-9.

Bouhassira, Didier et al., "Investigation of the Paradoxical Painful Sensation ('Illusion of Pain') Produced by a Thermal Grill," *Pain*, International Association for the Study of Pain, published by Elsevier, vol. 114, 2005, pp. 160-167.

Craig, A.D. and M.C. Bushnell, "The Thermal Grill Illusion: Unmasking the Burn of Cold Pain," *Science*, vol. 265, Jul. 8, 1994, pp. 252-255.

Del Campo, J. et al., "Antimicrobial Effect of Rosemary Extracts," *Journal of Food Protection*, vol. 63, No. 10, Oct. 2000, pp. 1359-1368.

Folwaczny, M. et al., "Antibacterial Effects of Pulsed Nd:YAG Laser Radiation at Different Energy Settings in Root Canals," *Journal of Endodontics*, vol. 28, No. 1, Jan. 2002, pp. 24-29.

Lange, N., "Thermodynamic Properties: Heats of Solution," *Lange's Handbook of Chemistry*, 11th Ed., McGraw-Hill Book Company, New York, 1973, pp. 9-107 to 9-115.

Martinez, M. et al., "Reduced Outer Membrane Permeability of *Escherichia Coli* O157:H7: Suggested Role of Modified Outer Membrane Porins and Theoretical Function in Resistance to Antimicrobial Agents," *Biochemistry*, vol. 40, No. 40, Oct. 9, 2001, pp. 11965-11970, 11972-11974.

Moro, M. et al., "Effects of Heat Stress on the Antimicrobial Drug Resistance of *Escherichia Coli* of the Intestinal Flora of Swine," *Journal of Applied Microbiology*, vol. 88, No. 5, May 2000, pp. 836-844.

Niwa, M. et al., "Differential Uptake of Grepafloxacin by Human Circulating Blood Neutrophils and Those Exudated into Tissues," *European Journal of Pharmacology*, vol. 428, No. 1, Sep. 28, 2001, pp. 121-126.

Raj, P. et al., "Synthesis, Microbicidal Activity, and Solution Structure of the Dodecapeptide from Bovine Neutrophils," *Biopolymers*, vol. 53, No. 4, Apr. 5, 2000, pp. 281-288, 290-292.

Yamaguchi, S. et al., "Orientation and Dynamics of an Antimicrobial Peptide in the Lipid Bilayer by Solid-State NMR Spectroscopy," *Biophysical Journal*, vol. 81, No. 4, Oct. 2001, pp. 2203-2214.

* cited by examiner

PATTERNED SELF-WARMING WIPE SUBSTRATES

FIELD

The present disclosure generally relates to wipes that are self-warming or become warm quickly after dispensing. More particularly, wipes having alternating patterned thermally active areas that provide a warming sensation for the entire wipe is disclosed.

BACKGROUND

Wet wipes and dry wipes and related products have been commonly used by consumers for various cleaning and wiping tasks. For example, many parents have utilized wet wipes to clean the skin of infants and toddlers before and after urination and/or defecation. Many types of wipes both wet and dry are currently commercially available for this purpose.

Today, many consumers are demanding that personal health care products, such as wet wipes, have the ability to not only provide their intended cleaning function, but also to deliver a comfort benefit to the user. In recent studies, it has been shown that baby wet wipes currently on the market are sometimes perceived to be uncomfortably cold upon application to the skin, particularly for newborns. To mitigate this problem, there have been many attempts to produce warming products to warm the wipes to comfort the wet wipe users from the inherent cool sensation given off by the contact of the moistened wipes with the skin.

Warming wipes have been developed utilizing different chemistries, including use of reduction/oxidation reactions or providing crystallization enthalpy of a supersaturated solution capable of imparting a temperature change on the wipes that will provide heat. However, one drawback of utilizing these certain chemistries is the amount needed to warm the wipe.

Additionally, it is known that a sensation of heat is elicited within an individual when the individual touches interlaced warm and cool bars with their skin. The sensations of discomfort and temperature and even pain have been analogized to the burning sensation that accompanies touching extremely cold objects.

One of the prevailing explanations of this warming sensation is that the perception of "heat" is a fusion of sensations resulting from simultaneous activation of warm and cool sensors within the body. Modern physiological findings have confirmed the existence of separate cutaneous receptors for warm and cool. It is interesting to note that the cutaneous receptors that are associated with a cold sensation appear to be activated by low and high temperatures.

A thermal grill is a device that includes interlaced or alternating warm and cool portions that are able to provide a warming sensation to an individual when the individual touches the interlaced warm and cool portions. The relative size, shape, design, configuration, temperature, and orientation of the interlaced warm and cool portions may be varied to adjust the level of discomfort that can be generated within an individual that touches the thermal grill with their skin. However, there is a need to provide a thermal grill that does not provide a feeling of discomfort, but a pleasant feeling of warmth.

Based on the foregoing, there is a need in the art for wipes that can produce a warming sensation just prior to, or at the point of use, without using external heating products by providing the minimum amount of heating chemistries necessary to provide a warming sensation for the entire wipe substrate. It would be desirable if the wipes would produce a warming sensation within less than about 10 seconds after activation and raise the temperature of the wet wipe solution and the wipe substrate at least 5° C. or more for at least 20 seconds.

SUMMARY

Generally stated, the present disclosure relates to wiping substrates such as wet wipes and dry wipes including a thermal grill that is used to deliver a warming sensation. In an exemplary aspect, disposed on at least one structural layer of the wipe substrate is a thermal grill. The thermal grill includes an alternating pattern of thermally active areas and secondary areas that provide a feeling of warmth to a user of the wipe across the entire surface of the wipe. The thermally active portions of the wipe include a temperature change substance adapted to provide a temperature change of at least 5° C. from the temperature of the secondary portion when placed in communication with an activation agent.

In an exemplary aspect, the thermally active portions of the wipe include a temperature change substance adapted to provide a temperature change of at least 5° C. from the temperature of the secondary portion. In another aspect, the thermally active portions of the wipe include an amount of the temperature change substance in communication with an activation agent to provide a temperature change of between about 5° C. and about 30° C. from the temperature of the secondary portion, and more particularly between 10° C. and about 15° C. from the temperature of the secondary portion.

In another aspect, the secondary portions of the wipe are at room temperature. Correspondingly, temperatures in the thermally active areas would range from about 30° C. and about 55° C., and more particularly range from about 35° C. and about 40° C.

In another aspect, the thermally active portions and secondary portions form a pattern of bars extending substantially the entire length of the wipe. In an exemplary aspect, each thermally active portion has a width of about 0.05 centimeters to about 2 centimeters. In an exemplary embodiment, the width of the thermally active portion is substantially the same as the width of the secondary portion. In another embodiment, the width of the thermally active portions is between 50% to about 200% of the width of the secondary portions. For example, if each thermally active portion forms a bar pattern extending the length of the wipe having a width of about 1.0 centimeters then each secondary portion forms a bar pattern extending the length of the wipe having a width of about 1.0 centimeters.

In another aspect, the thermal grill contains at least two thermally active portions with at least one secondary portion between the at least two thermally active portions.

In an exemplary aspect, thermally active areas comprise a temperature change substance in liquid communication with an activation agent capable of imparting a temperature change to the products through an exothermic reaction. In one example, the temperature change substance and activation agent are topically applied to the thermally active area. In another aspect, the thermally active portions include an encapsulated composition containing the activation agent, and wherein upon rupture of the encapsulated portion, a reaction occurs between the activation agent and the temperature change substance.

In exemplary aspects, the temperature change substance is a supersaturated solution prepared from an aqueous solution of a salt, the salt being selected from the group consisting of sodium acetate, sodium sulfate, sodium thiosulfate, potash alum, calcium nitrate, potassium acetate, ammonium nitrate, potassium nitrate, lithium acetate, magnesium acetate, chromium alum, sodium carbonate, magnesium sulfate, sodium borate, sodium bromide, sodium chromate, calcium chloride, magnesium chloride, magnesium nitrate, disodium phosphate, urea nitrate, and hydrates thereof. To initiate the reaction an activation agent may be selected from the group consisting of sodium acetate, sodium sulfate, sodium sulfate decahydrate, sodium thiosulfate, potash alum, calcium nitrate, potassium acetate, ammonium nitrate, potassium nitrate, lithium acetate, magnesium acetate, chromium alum, sodium carbonate, magnesium sulfate, sodium borate, sodium bromide, sodium chromate, calcium chloride, magnesium chloride, magnesium nitrate, disodium phosphate, urea nitrate, and hydrates thereof. For example, a supersaturated solution may be encapsulated in the thermally active portions of an interior layer of the wipe, and wherein upon rupture of the encapsulated portion, an activation agent initiates a phase change in the supersaturated salt solution, causing it to crystallize, and imparts a temperature change to the thermally active potions.

In another exemplary aspect, the temperature change substance could be an aqueous solution having an oxidizing agent in liquid communication with a reducing agent, wherein a reaction occurs between the oxidizing agent and the reducing agent imparting a temperature change to the thermally active portions.

The oxidizing agent may be selected from hydrogen peroxide, sodium percarbonate, carbamide peroxide, ammonium persulfate, calcium peroxide, ferric chloride, magnesium peroxide, melamine peroxide, phthalimidoperoxycaproic acid, potassium bromate, potassium caroate, potassium chlorate, potassium persulfate, potassium superoxide, PVP-hydrogen peroxide, sodium bromate, sodium chlorate, sodium chlorite, sodium hypochlorite, sodium iodate, sodium perborate, sodium persulfate, strontium peroxide, urea peroxide, zinc peroxide, benzoyl peroxide, sodium peroxide, sodium carbonate, and barium peroxide. The reducing agent is selected from the group consisting of sodium ascorbate, sodium erythrobate, sodium sulfite, sodium bisulfite, thiourea, ammonium bisulfite, ammonium sulfite, ammonium thioglycolate, ammonium thiolactate, cysteamine hydrochloride, cysteine, cysteine hydrochloride, dithiothreitol, ethanolamine thioglycolate, glutathione, glyceryl thiopropionate, hydroquinone, p-hydroxyanisole, isooctyl thioglycolate, mercaptopropionic acid, potassium metabisulfite, potassium sulfite, potassium thioglycolate, sodium hydrosulfite, sodium hydroxymethane sulfonate, sodium metabisulfite, sodium thioglycolate, sodium tocopheryl phosphate, strontium thioglycolate, superoxide dismutase, thioglycerin, thioglycolic acid, thiolactic acid, thiosalicylic acid, thiosulfate salts, borohydride salts, hypophosphite salts, ascorbic acid and salts, tocopherol salts, esters, aluminum powder, and magnesium powder.

In a further exemplary aspect, the temperature change substance may be an ionic salt in liquid communication with an active metal wherein a metal ion replacement reaction occurs between an ionic salt and the active metal imparting a temperature change to the thermally active portions. The ionic salt may be selected from the group consisting of, but not limited to, copper chloride, copper oxide, and copper acetate. The active metal may be selected from the group consisting of aluminum and magnesium.

BRIEF DESCRIPTION

Figure 2:
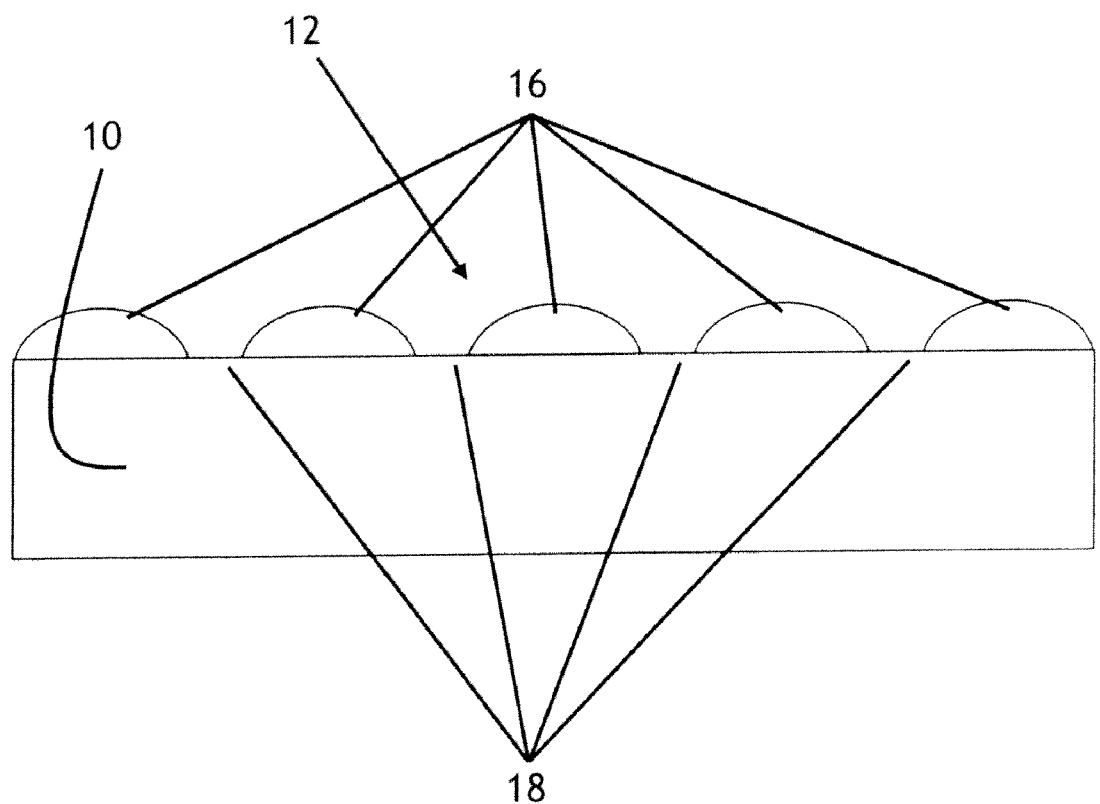

FIG. 1 illustrates a plan view of an exemplary wipe substrate of the present disclosure; and FIG. 2 illustrates a cross sectional view of the wipe substrate shown in FIG. 1.

DETAILED DESCRIPTION

It is to be understood by one of ordinary skill in the art that the present discussion is a description of exemplary embodiments only, and is not intended as limiting the broader aspects of the present disclosure.

The present disclosure relates to wiping substrates such as wet wipes and dry wipes including a thermal grill that is used to deliver a warming sensation. Disposed on at least one structural layer of the wipe substrate is a thermal grill. The thermal grill includes an alternating pattern of thermally active areas and secondary areas that provide a feeling of warmth to a user of the wipe across the entire surface of the wipe. The thermally active portions of the wipe include a temperature change substance adapted to provide a temperature change of at least 5° C. from the temperature of the secondary portion. Surprisingly, it has been found that when incorporating a thermal grill into a wipe and then allowing a user to come into contact upon wipe use, the entire wipe provides a warming sensation to allow for a comforting feel to the skin.

Referring to FIGS. 1 and 2, an exemplary wipe substrate 10 of the present disclosure is illustrated. As used herein a wipe substrate is a flexible sheet or web material, which is useful for household chores, personal care, health care, food wrapping, and cosmetic application or removal. Non-limiting examples of suitable substrates of the present invention include nonwoven substrates, woven substrates, hydro-entangled substrates, air-entangled substrates, paper substrates such as tissue, toilet paper, or paper towels, waxed paper substrates, coform substrates, wet wipes, film or plastic substrates such as those used to wrap food, and metal substrates such as aluminum foil. Furthermore, laminated or plied together multi-layer substrates of two or more layers of any of the preceding substrates are suitable.

In an exemplary aspect, the wipe substrate of the pending disclosure is a nonwoven substrate. Nonwoven substrates can be formed by a variety of known forming processes, including airlaying, meltblowing, spunbonding, or bonded carded web formation processes. "Airlaid" refers to a porous web formed by dispersing fibers in a moving air stream prior to collecting the fibers on a forming surface. The collected fibers are then typically bonded to one another using, for example, hot air or a spray adhesive. Suitable examples of airlaid webs can be found in U.S. Pat. No. 5,486,166 issued to Bishop et al., U.S. Pat. No. 6,960,349 issued to Shantz et al., and U.S. Publication No. 2006/0008621 to Gusky et al., all incorporated by reference to the extent that they are consistent herewith.

The fibrous nonwoven substrate material may also comprise meltblown materials. "Meltblown" refers to fibers formed by extruding a molten thermoplastic material through a plurality of fine, usually circular, die capillaries as molten threads or filaments into converging high velocity gas (e.g., air) streams, generally heated, which attenuate the filaments of molten thermoplastic material to reduce their diameters. Thereafter, the meltblown fibers are carried by the high velocity gas stream and are deposited on a collecting surface or support to form a web of randomly dispersed meltblown fibers. Such a process is disclosed, for example, in U.S. Pat. No. 3,849,241 to Butin et al. Meltblowing processes can be used to make fibers of various dimensions, including macrofibers (with average diameters from about 40 to about 100 microns), textile-type fibers (with average diameters between about 10 and 40 microns), and microfibers (with average diameters of less than about 10 microns). Meltblowing processes are particularly suited to making microfibers, including ultra-fine microfibers (with an average diameter of about 3 microns or less). A description of an exemplary process of making ultra-fine microfibers may be found in, for example, U.S. Pat. No. 5,213,881 to Timmons et al. Meltblown fibers may be continuous or discontinuous and are generally self bonding when deposited onto a collecting surface.

"Spunbonded fibers" refers to small diameter fibers which are formed by extruding molten thermoplastic material as filaments from a plurality of fine, usually circular capillaries of a spinneret with the diameter of the extruded filaments then being rapidly reduced to fibers as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, and U.S. Pat. No. 3,542,615 to Dobo et al., the contents of which are incorporated herein by reference in their entirety. Spunbond fibers are generally continuous and have diameters generally greater than about 7 microns, more particularly, between about 10 and about 20 microns.

"Bonded-carded web" refers to a web made from staple fibers sent through a combing or carding unit, which separates or breaks apart and aligns the fibers to form a nonwoven web. For example, the web may be a powder bonded carded web, an infrared bonded carded web, or a through-air bonded carded web. Examples of such materials may be found in U.S. Pat. No. 5,490,846 to Ellis et al.; U.S. Pat. No. 5,364,382 to Latimer; and U.S. Pat. No. 6,958,103 to Anderson et al.

Disposed on at least one structural layer of the wipe substrate 10 is a thermal grill. The thermal grill 12 is a device that has one or more thermally active portions 16 that are interlaced or alternated with one or more secondary portions 18. When the thermally active portions 116 are activated and an individual contacts the thermal grill 12, the temperature differences between thermally active portions 16 and secondary portions 18 of the thermal grill 12 cause the individual to feel a warm sensation across the entire width of the wipe substrate 10. The relative size, shape, design, configuration, temperature, and orientation of the interlaced thermally active portions 16 and secondary portions 18 may be varied in order to adjust the level of warmth that can be generated within an individual that touches the thermal grill 12 with their skin. In addition, thermally active portions 16 and secondary portions 18 may be positioned in a generally horizontal orientation as shown in FIG. 1, in a generally vertical orientation, or in any other suitable orientation. Additionally, the thermally active portions 16 may be applied in alternating stripes, a checkerboard pattern, a concentric pattern of aligned circles or other shapes, or any other suitable geometric or non-geometric pattern.

As used herein, the term thermally active portion and its plural refer to the portion of the thermal grill that is exothermic or potentially exothermic. The thermally active portions 16 may actually feel warm as it does upon activation, or the thermally active portions 16 may be potentially warm or warmable as it is before activation in that it includes material that will give off heat upon activation. Likewise, as used herein, the term secondary portion 18 and its plural refer to the portion of the thermal grill 12 that is unaltered, is endothermic or potentially endothermic. The secondary portions 18 may actually be at room temperature, feel cool as it does upon activation, or the secondary portions 18 may be potentially cool or coolable as it is before activation in that it includes material that will absorb heat upon activation.

It is generally the case that the greater the temperature differences between the thermally active portions 16 and secondary portions 18, the greater the probability that the user or the child will experience consequential discomfort. A temperature difference in the range of between about 5 to 10° C. is where a warming sensation typically begins to be experienced. At higher temperature differences, the intensity of the discomfort response and the percent of users who will have an uncomfortably warm feeling increases (see Bouhassira et al., "Investigation of the Paradoxical Painful Sensation ('Illusion of Pain') Produced by a Thermal Grill"—Pain 114 (2005) 160-167). As a result, the configuration and amount of temperature change substance on the thermally active portions 16 and secondary portions 18 may be varied in order to adjust the level of warmth that can be generated within an individual that touches the thermal grill 12 with their skin.

In another aspect, an amount of heating chemistry is added to the thermally active portions of the thermal grill 12 to provide warmer areas of the wipe. In an exemplary aspect, the thermally active portions 16 include a temperature change substance and an activation agent in liquid communication to provide a temperature change of at least 5° C. from the temperature of the secondary portion. More particularly, an amount of the temperature change substance is included to provide a temperature change of between about 5° C. and about 30° C. from the temperature of the secondary portion, and more particularly, an amount of the temperature change substance is added to provide a temperature change of between about 15° C. and about 20° C. from the temperature of the secondary portion. In an exemplary embodiment, the secondary portions of the wipe substrate will be at room temperature, typically about 20 to 22° C. Therefore, temperatures in the thermally active areas would range from about 30° C. and about 45° C., and more particularly range from about 35° C. and about 40° C.

Similarly, the width and spacing of the thermally active portions 16 and secondary portions 18 in the wipe substrate 10 may be varied to give the correct warming sensation to the user. In an exemplary aspect, the thermally active portions form a pattern of bars extending the length of the wipe having a width of between about 0.05 centimeters to 2 centimeters. In an exemplary embodiment, the width of the thermally active portion is substantially the same as the width of the secondary portion. In another embodiment, the width of the thermally active portions is between 50% to about 200% of the width of the secondary portions. For example, if each thermally active portion forms a bar pattern extending the length of the wipe having a width of about 1.0 centimeters and each secondary portion forms a bar pattern extending the length of the wipe having a width of about 1.0 centimeters.

Generally, the wipe substrates have one or more structural layers comprising similar or different materials. In one aspect, the thermal grill 12 is positioned on the structural layer in a location most likely to be in contact with the user, or an exterior surface of the wipe substrate 10. In another aspect, the thermal grill 12 may be placed on both sides of the wipe substrate. In still other aspects, the thermal grill 12 may be placed on an inner structural layer. The positioning of the thermal grill 12 can be on any structural layer as the heat provided by the thermal grill 12 applied to one exterior surface of the wipe effectively transfers through the wipe to the opposing side. The amount of temperature change substance that is provided depends on the chemistries involved and the amount of heat necessary to raise the temperature the specified amounts.

In one aspect of the present invention, the thermally active portions 16 of the thermal grill 12 are formed by applying alternating stripes of a temperature change substance to one of the structural layers of the wipe substrate 10. In various aspects, the temperature change substance may be applied to a thermally active area 16 by blending into a lotion which is then applied to one of the structural layers, such as the exterior surface of the wipe substrate. In another aspect, the temperature change substance may also be combined into a liquid concentrated solution and sprayed onto the structural layer. In still another aspect, the temperature change substance may be produced in crystalline form and sprinkled or otherwise applied to the structural layer, using a suitable adhesive if desired. In any of these aspects, the thermally active portions 16 may be applied in alternating stripes, a checkerboard pattern, a concentric pattern of aligned circles or other shapes, or any other suitable geometric or non-geometric pattern. Similarly, the thermally active portions may be colored using inks, dyes, or any other suitable substance to illustrate the thermal grill.

In terms of the temperature change aspect of the thermally active areas 16 of the wipe substrate 10, the temperature change substance provides a surface temperature change of from between about 5 and about 30° C. More desirably, the temperature change substance provides a surface temperature change when wet of from between about 10° C. to about 20° C., and particularly between about 15° C. for improved performance. Also, the warm sensation produced by the thermally active areas 16 should last from about 1 to about 120 seconds, and particularly from about 10 to about 60 seconds, such as about 30 seconds.

A suitable procedure for determining the surface temperature change of the wipe substrate containing thermally active areas with a temperature change substance is as follows. The test should be conducted in an environment having a stable temperature of 21 to 22° C. and a stable humidity of about 50 percent. The surface temperature of the wipe substrate at the location of the temperature change substance and at the location of the secondary portions is measured by utilizing a standard infrared video imaging camera. Video images are taken of the wipe substrate to illustrate the surface temperature at 20 second intervals during the first 120 second after the temperature change substance is activated and the peak temperature values of each thermally active portion and each secondary portion are recorded.

In one exemplary aspect, encapsulation, or any suitable means for delaying of the activating agent being in communication with the temperature change substance, may be used to delay the temperature change until desired by a user. Specifically, the activation agent can be included in an encapsulated composition and the temperature change substance can be included in an aqueous solution, or vice versa. A consumer would rupture the encapsulated activation agent by applying pressure to produce a reaction or initiate a phase change. Once ruptured, the contents of the encapsulated activation agent react with a temperature change substance in the aqueous solution, causing a reaction that results in the heating of the thermally active areas of the wipe substrate.

The encapsulated composition may include an encapsulation layer that substantially completely surrounds the activation agent or temperature change substance. The encapsulation layer allows the activation agent to be separate from the temperature change substance until activation by the user.

Generally, the encapsulation layer may include a crosslinked polymeric material. For example, the encapsulation layer may be comprised of a polymeric material, a crosslinked polymeric material, a metal, a ceramic or a combination thereof, that results in a shell material that may be formed during manufacturing. Specifically, the encapsulation layer may be comprised of superabsorbent materials, crosslinked sodium alginate, anionic dispersed latex emulsions, crosslinked polyacrylic acid, crosslinked polyvinyl alcohol, crosslinked polyvinyl acetate, silicates, carbonates, sulfates, phosphates, borates, polyvinyl pyrolidone, PLA/PGA, thermoionic gels, urea formaldehyde, melamine formaldehyde, polymelamine, crosslinked starch, nylon, ureas, hydrocolloids, and combinations thereof.

In another exemplary aspect, a lotion including the encapsulated activation agents is held in the dispenser separately from the wet wipe until the wet wipe is dispensed from the system. When the lotion including the activation agents is held separately from the wet wipe (and the aqueous wet wipe solution present on the wet wipe) until the wet wipe is dispensed, one advantage realized is that there is a significantly reduced chance of heating the wipe substrate before the desired time; that is, because the activation agents are held in a container separate from the aqueous solution of the wet wipe, the heating agent cannot contact the aqueous solution prior to mixing and lose potency prior to use. In an exemplary aspect, a wet wipe container including a cartridge configured to further define a lotion container formed integrally therewith and having an internal compartment for containing a lotion may be utilized. A lotion may be disposed within the internal compartment such that the lotion is out of contact with the wipes in the wipe container.

In another aspect, the lotion including the activation agent is held separately from the wipe, and therefore separately from the aqueous solution held on the wipe, until just prior to use, so that the activation agent could be introduced into the wipe substrate. Because the lotions are generally non-aqueous based, the heating agent can survive over time in the lotions without losing potency as there is no available water for the activation agent to react with. Once dispensed onto the wipe including the aqueous wet wipe solution, the activation agent can react with the water to produce heat without any need for rupturing of an encapsulated shell.

The cartridge on the dispenser generally may comprise an applicator that communicates with the internal compartment of the lotion container and is operable to apply lotion from the container onto a wipe as the wipe is dispensed from a slot in the cartridge. For example, rollers provided for generally free rotation relative to the lotion container may be configured to sealingly seat the roller in the lotion container so that a portion of the roller surface is disposed within the internal compartment of the lotion container, in contact with the lotion in the container, and the remaining portion of the roller surface is disposed exterior of the lotion container to double as part of the activating member as well.

Upon rotation of the roller, lotion coats the surface of the portion of the roller within the internal compartment and the coated portion is rotated exterior of the roller for transferring the lotion from the coated portion of the roller onto a wipe in a pattern creating a thermal grill as described above as the wet wipe passes through the nip formed between the rollers.

Suitable temperature change substances provide heat through a chemical reaction or phase change when put in communication with an activation agent. One exemplary temperature change substance for use with the present disclosure is a supersaturated solution. The supersaturated solution, upon activation and contact with an activation agent, is capable of evolving heat and causing a warming sensation on the skin of a user of the wipe. In one aspect, the activation agent is included in a core layer that may optionally include one or more encapsulating layers.

As noted above, the wipes may contain a composition comprising a supersaturated solution. Supersaturated solutions can be formed by heating aqueous solutions to a temperature of suitably from about 30° C. to about 100° C., and more suitably, from about 32° C. to about 90° C., and dissolving particles (e.g., salts or sugars) in the heated aqueous solutions. Typically, the aqueous solutions are made up of water. Under these heated conditions, more particles are capable of dissolving in the solutions, and upon cooling, a supersaturated solution is formed. These supersaturated solutions are unstable and will completely crystallize if exposed to an activation means such as a nucleation site (e.g., a seed crystal) as described more fully below. As the solute from the supersaturated solution crystallizes, heat is produced through crystallization enthalpy or latent heat of fusion.

Suitable supersaturated solutions, therefore, are capable of producing a high crystallization enthalpy and a high crystallization rate. Generally, the supersaturated solutions are capable of generating a crystallization enthalpy of at least about 70 Joules/gram, and more suitably at least about 125 Joules/gram. In one embodiment, the supersaturated solutions are capable of generating a crystallization enthalpy of from about 70 Joules/gram to about 500 Joules/gram. Additionally, the supersaturated solutions suitably produce a crystallized solid product having a crystallization rate, that is the rate at which the solution crystallizes, of at least about 0.01 centimeters/second, more suitably at least about 0.03 centimeters/second, even more suitably, at least about 0.05 centimeters/second, and even more suitably at least about 0.10 centimeters/second.

Additionally, the supersaturated solution for use in the wet wipes according to one embodiment suitably has a crystallization temperature of from about 25° C. to about 90° C. More suitably, the supersaturated solution has a crystallization temperature of from about 30° C. to about 60° C. supersaturated solutions with these crystallization temperatures are capable of warming the wipe to a level of giving the perception of warmth without overheating the wipe to risk skin burns.

One particularly suitable example is a supersaturated solution of sodium acetate. Specifically, to produce a supersaturated solution of sodium acetate, a solution of sodium acetate and water is heated to a temperature of greater than about 58° C. and allowed to slowly cool to room temperature. The resulting supersaturated solution of sodium acetate will crystallize once it comes into contact with an activation means such as a sodium acetate seed crystal. The supersaturated sodium acetate solution is capable of generating a crystallization enthalpy of 264 Joules/gram, and thus, will produce a temperature to heat the thermally active areas of the wipe substrate from about 50° C. to about 60° C. The generation of this amount of heat will generally lead to an increase in wet wipe temperature of approximately 15° C. to 20° C. Additionally, the supersaturated solution will produce a crystallized product, sodium acetate trihydrate, having a crystallization rate of as high as about 0.68 centimeters/second.

Other suitable supersaturated solutions for use in the wipes of the present disclosure include, for example, supersaturated solutions prepared from aqueous solutions of salts or sugars, the salt or sugar being selected from the group consisting of sodium sulfate, sodium thiosulfate, potash alum, calcium nitrate, potassium acetate, ammonium nitrate, potassium nitrate, lithium acetate, magnesium acetate, chromium alum, sodium carbonate, magnesium sulfate, sodium borate, sodium bromide, sodium chromate, calcium chloride, magnesium chloride, magnesium nitrate, disodium phosphate, urea nitrate, and hydrates thereof.

Typically, the activation means is comprised of one or more seed crystals having a similar chemistry as compared to the supersaturated solution. More particularly, a suitable activation means will have crystallographic data being within about 15% of that of the material to be crystallized in the supersaturated solution. As such, in the embodiment wherein the supersaturated solution is a supersaturated salt solution, the activation means is suitably a salt selected from the group consisting of sodium acetate, sodium sulfate, sodium sulfate decahydrate, sodium thiosulfate, potash alum, calcium nitrate, potassium acetate, ammonium nitrate, potassium nitrate, lithium acetate, magnesium acetate, chromium alum, sodium carbonate, magnesium sulfate, sodium borate, sodium bromide, sodium chromate, calcium chloride, magnesium chloride, magnesium nitrate, disodium phosphate, urea nitrate, and hydrates thereof.

For example, a supersaturated solution may be encapsulated in the thermally active portions of an interior layer of the wipe, and wherein upon rupture of the encapsulated portion, an activation agent initiates a phase change in the supersaturated salt solution, causing it to crystallize, and imparts a temperature change to the thermally active potions.

In another aspect, the reaction is caused by an oxidizing agent and a reducing agent coming into contact within the wipe substrate. As noted above, in one particularly suitable embodiment, the reactive chemistry is a reduction/oxidation reaction, involving an oxidizing agent and a reducing agent. When the oxidizing agent contacts the reducing agent, a reduction/oxidation reaction occurs that can generate heat, gas, or a combination thereof.

An oxidizing agent is the chemical reactant of the reduction/oxidation reaction that readily gains electrons. Suitable oxidizing agents include, for example, hydrogen peroxide, sodium percarbonate, carbamide peroxide, ammonium persulfate, calcium peroxide, ferric chloride, magnesium peroxide, melamine peroxide, phthalimidoperoxycaproic acid, potassium bromate, potassium caroate, potassium chlorate, potassium persulfate, potassium superoxide, PVP-hydrogen peroxide, sodium bromate, sodium chlorate, sodium chlorite, sodium hypochlorite, sodium iodate, sodium perborate, sodium persulfate, sodium perborate monohydrate, strontium peroxide, urea peroxide, zinc peroxide, benzoyl peroxide, sodium peroxide, sodium carbonate, barium peroxide, alkyl metal salts of perborates, and carbonate-peroxides.

In addition to the oxidizing agent, the reduction/oxidation reaction requires a reducing agent. The reducing agent is the reactant that reduces the oxidizing agent; that is the reactant of the reduction/oxidation reaction that donates electrons to the oxidizing agent. Typically, the reducing agent can be incorporated either into a microencapsulated composition or included in an aqueous solution, as long as the oxidizing agents described above do not contact the reducing agents until the desired point of use.

As noted above, the reactive chemistries can be incorporated into an aqueous solution or into a microencapsulated composition. In determining whether to incorporate specific reactants into the microencapsulated composition or into the aqueous solution, the primary factor to consider is whether or not the specific reactant is stable in the aqueous solution. Specifically, when the reactive chemistry is a reduction/oxidation reaction using hydrogen peroxide as the oxidizing agent and sodium sulfite as the reducing agent, hydrogen peroxide is included in an aqueous solution and sodium sulfite is incorporated into a microencapsulated composition as sodium sulfite has been found to be unstable when in an aqueous solution and further when in contact with the pulp fibers within the basesheet of a wipe substrate such as a wet wipe.

Suitable reducing agents for use in the wipe substrates of the present disclosure include, for example, sodium ascorbate, sodium erythrobate, sodium sulfite, sodium bisulfite, thiourea, ammonium bisulfite, ammonium sulfite, ammonium thioglycolate, ammonium thiolactate, cysteamine hydrochloride, cysteine, cysteine hydrochloride, dithiothreitol, ethanolamine thioglycolate, glutathione, glyceryl thiopropionate, hydroquinone, p-hydroxyanisole, isooctyl thioglycolate, mercaptopropionic acid, potassium metabisulfite, potassium sulfite, potassium thioglycolate, sodium hydrosulfite, sodium hydroxymethane sulfonate, sodium metabisulfite, sodium thioglycolate, sodium tocopheryl phosphate, strontium thioglycolate, superoxide dismutase, thioglycerin, thioglycolic acid, thiolactic acid, thiosalicylic acid, thiosulfate salts, borohydride salts, hypophosphite salts, ascorbic acid, ascorbic salts, ascorbic esters, and ascorbic derivatives (e.g., ascorbyl palmitate and ascorbyl polypeptide), tocopherol salts, tocopherol esters, and tocopherol derivatives (e.g., tocopherol acetate), aluminum powder, and magnesium powder.

Alternatively, the reactive chemistry is a metal ion replacement reaction. During a metal ion replacement reaction, a more active metal replaces a less active metal ion from the solution, generating heat as a byproduct. A suitable example is contacting an aluminum powder with a copper(II) chloride salt solution. The aluminum replaces the copper ion in the salt solution.

Suitable metals for use as the active metal in the metal ion replacement reaction include aluminum and magnesium. Suitable ionic salts that are capable of undergoing metal ion replacement include copper chloride, copper oxide, and copper acetate.

The present disclosure is illustrated by the following examples which are merely for the purpose of illustration and are not to be regarded as limiting the scope of the disclosure or manner in which it may be practiced.

EXAMPLE 1

A multiple layer wipe having an area of approximately 290 centimeters$^2$ was prepared comprising about 70% pulp fiber and 30% melt-blown fibers and an aqueous wet wipe solution was added to the sheet. A strip of plastic film was placed over the wipe and a warming lotion was applied to the wipe substrate with a roller creating a patterned thermal grill on the wipe. The warming lotion comprises a magnesium chlorides temperature change substance and mineral oil applied to the surface of the wipe. In this example, heat is generated when the water in the wipe combines with the magnesium chloride in the warming lotion.

Approximately 1.2 grams of the warming lotion was applied to the wipe substrate covering approximately 35% of the wipe. Therefore, approximately 9.5 mg/centimeters$^2$ of the warming lotion was added to the wipe. Images were taken utilizing an infrared camera and illustrated localized maximum temperatures of between 39 and 49° C. There was little heat distribution away from the area of application. However, due to the effect of the thermal grill, the entire wipe substrate gave the sensation of warmth upon touching of the wipe.

EXAMPLE 2

A multiple layer wipe having an area of approximately 290 centimeters$^2$ was prepared comprising about 70% pulp fiber and 30% melt-blown fibers and an aqueous wet wipe solution was added to the sheet. A strip of plastic film was placed over the wipe and a warming lotion was applied to the wipe substrate with a roller creating a patterned thermal grill on the wipe. The warming lotion comprises a magnesium chlorides temperature change substance and mineral oil applied to the surface of the wipe. In this example, heat is generated when the water in the wipe combines with the magnesium chloride in the warming lotion.

Approximately 2.4 grams of the warming lotion was applied to approximately 35% of the wipe. Therefore, approximately 18 mg/centimeters$^2$ of the warming lotion was added to the wipe. Images were taken utilizing an infrared camera and illustrated localized maximum temperatures of between 51 and 57° C. The temperature provided by this example is extremely warm and illustrates how the concentration of the warming lotion affects the temperature of the thermally active portions. Similar to example 1, there was little heat distribution away from the area of application. However, due to the effect of the thermal grill, the entire wipe substrate gave the sensation of warmth upon touching of the wipe.

In a preferred embodiment illustrated by the two examples, the amount of add-on lotion including temperature change substance provided for the thermally active areas of the wipe substrate may be between about 8 mg/centimeters$^2$ and 15 mg/centimeters$^2$ of an anhydrous magnesium chloride warming lotion and mineral oil.

When introducing elements of the present disclosure, the articles "a", "an", "the" and "said" are intended to mean that there are one or more of the elements. The terms "comprising", "including" and "having" are intended to be inclusive and mean that there may be additional elements other than the listed elements.

As various changes could be made in the above formulations and products without departing from the scope of the disclosure, it is intended that all matter contained in the above description shall be interpreted as illustrative and not in a limiting sense.

The invention claimed is:

1. A wipe substrate comprising a thermal grill disposed on at least one structural layer of the wipe substrate, wherein the wipe substrate is selected from nonwoven substrates, woven substrates, hydro-entangled substrates, air-entangled substrates, and coform substrates; the wipe substrate having an external surface, the thermal grill comprising an alternating pattern of a thermally active portions and secondary portions, the thermally active portions comprising a temperature change substance and an activation agent in liquid communication to provide a temperature change of at least 5° C. from the temperature of the secondary portion; wherein the secondary portions are at room temperature.

2. The wipe substrate of claim 1 wherein the thermally active portions include an amount of the temperature change substance to provide a temperature change of between about 5° C. and about 30° C. from the temperature of the secondary portion.

3. The wipe substrate of claim 1 wherein the thermally active portions include an amount of the temperature change substance to provide a temperature change of between about 10° C. and about 15° C. from the temperature of the secondary portion.

4. The wipe substrate of claim 1 wherein the thermally active portions and secondary portions form a pattern of bars extending substantially the entire length of the wipe.

5. The wipe substrate of claim 4 wherein each thermally active portion has a width of about 0.05 centimeters to about 2 centimeters.

6. The wipe substrate of claim 1 wherein each thermally active portion forms a bar extending the length of the wipe having a width of between about 50% and 200% of the width of a bar formed by each secondary portion.

7. The wipe substrate of claim 1 wherein the thermal grill contains at least two thermally active portions with at least one secondary portion between the at least two thermally active portions.

8. The wipe substrate of claim 1 wherein the temperature change substance comprises a supersaturated solution in liquid communication with an activation agent capable of imparting a temperature change to the products through crystallization enthalpy.

9. The wipe substrate of claim 1, wherein the temperature change substance and the activation agent are topically applied to the thermally active area.

10. The wipe substrate of claim 1, wherein the thermally active portions further comprise an encapsulated composition containing the activation agent, and wherein upon rupture of the encapsulated portion, a reaction occurs between the activation agent and the temperature change substance.

11. The wipe substrate of claim 9, wherein the supersaturated solution is a supersaturated salt solution prepared from an aqueous solution of a salt, the salt being selected from the group consisting of sodium acetate, sodium sulfate, sodium thiosulfate, potash alum, calcium nitrate, potassium acetate, ammonium nitrate, potassium nitrate, lithium acetate, magnesium acetate, chromium alum, sodium carbonate, magnesium sulfate, sodium borate, sodium bromide, sodium chromate, calcium chloride, magnesium chloride, magnesium nitrate, disodium phosphate, urea nitrate, and hydrates thereof.

12. The wipe substrate of claim 9, wherein the activation agent is selected from the group consisting of sodium acetate, sodium sulfate, sodium sulfate decahydrate, sodium thiosulfate, potash alum, calcium nitrate, potassium acetate, ammonium nitrate, potassium nitrate, lithium acetate, magnesium acetate, chromium alum, sodium carbonate, magnesium sulfate, sodium borate, sodium bromide, sodium chromate, calcium chloride, magnesium chloride, magnesium nitrate, disodium phosphate, urea nitrate, and hydrates thereof.

13. A wipe substrate of claim 1 wherein the temperature change substance comprises an aqueous solution having an oxidizing agent in liquid communication with a reducing agent.

14. The wipe substrate of claim 13 wherein the oxidizing agent is selected from the group consisting of hydrogen peroxide, sodium percarbonate, carbamide peroxide, ammonium persulfate, calcium peroxide, ferric chloride, magnesium peroxide, melamine peroxide, phthalimidoperoxycaproic acid, potassium bromate, potassium caroate, potassium chlorate, potassium persulfate, potassium superoxide, PVP-hydrogen peroxide, sodium bromate, sodium chlorate, sodium chlorite, sodium hypochlorite, sodium iodate, sodium perborate, sodium persulfate, strontium peroxide, urea peroxide, zinc peroxide, benzoyl peroxide, sodium peroxide, sodium carbonate, and barium peroxide.

15. The wipe substrate of claim 14 wherein the reducing agent is selected from the group consisting of sodium ascorbate, sodium erythrobate, sodium sulfite, sodium bisulfite, thiourea, ammonium bisulfite, ammonium sulfite, ammonium thioglycolate, ammonium thiolactate, cysteamine hydrochloride, cysteine, cysteine hydrochloride, dithiothreitol, ethanolamine thioglycolate, glutathione, glyceryl thiopropionate, hydroquinone, p-hydroxyanisole, isooctyl thioglycolate, mercaptopropionic acid, potassium metabisulfite, potassium sulfite, potassium thioglycolate, sodium hydrosulfite, sodium hydroxymethane sulfonate, sodium metabisulfite, sodium thioglycolate, sodium tocopheryl phosphate, strontium thioglycolate, superoxide dismutase, thioglycerin, thioglycolic acid, thiolactic acid, thiosalicylic acid, thiosulfate salts, borohydride salts, hypophosphite salts, ascorbic acid and salts, tocopherol salts, esters, aluminum powder, and magnesium powder.

16. The wipe substrate of claim 1 wherein the temperature change substance comprises an ionic salt in liquid communication with an active metal.

17. The wipe substrate of claim 16 wherein the ionic salt is selected from the group consisting of copper chloride, copper oxide, and copper acetate.

18. The wipe substrate of claim 16 wherein the active metal is selected from the group consisting of aluminum and magnesium.

* * * * *

UNITED STATES PATENT AND TRADEMARK OFFICE
CERTIFICATE OF CORRECTION

PATENT NO. : 7,924,142 B2  
APPLICATION NO. : 12/217043  
DATED : April 12, 2011  
INVENTOR(S) : Jason C. Cohen et al.

Page 1 of 1

It is certified that error appears in the above-identified patent and that said Letters Patent is hereby corrected as shown below:

Claim 15, Col. 14, lines 14-30 should read,

15. The wipe substrate of claim 13 wherein the reducing agent is selected from the group consisting of sodium ascorbate, sodium erythrobate, sodium sulfite, sodium bisulfite, thiourea, ammonium bisulfite, ammonium sulfite, ammonium thioglycolate, ammonium thiolactate, cysteamine hydrochloride, cysteine, cysteine hydrochloride, dithiothreitol, ethanolamine thioglycolate, glutathione, glyceryl thiopropionate, hydroquinone, p-hydroxyanisole, isooctyl thioglycolate, mercaptopropionic acid, potassium metabisulfite, potassium sulfite, potassium thioglycolate, sodium hydrosulfite, sodium hydroxymethane sulfonate, sodium metabisulfite, sodium thioglycolate, sodium tocopheryl phosphate, strontium thioglycolate, superoxide dismutase, thioglycerin, thioglycolic acid, thiolactic acid, thiosalicylic acid, thiosulfate salts, borohydride salts, hypophosphite salts, ascorbic acid and salts, tocopherol salts, esters, aluminum powder, and magnesium powder.

Signed and Sealed this  
Twenty-third Day of August, 2011

David J. Kappos  
*Director of the United States Patent and Trademark Office*